(12) United States Patent
Moriguchi et al.

(10) Patent No.: US 6,239,111 B1
(45) Date of Patent: *May 29, 2001

(54) IN VIVO METHOD OF IMPROVING SURVIVAL RATE OF BRAIN NEURONS

(75) Inventors: Toru Moriguchi; Hiromichi Matsuura, both of Hiroshima; Hiroshi Saito, Tokyo, all of (JP)

(73) Assignee: Wakunaga Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 13 days.

(21) Appl. No.: 08/983,322
(22) PCT Filed: May 23, 1997
(86) PCT No.: PCT/JP97/01733
   § 371 Date: Jan. 26, 1998
   § 102(e) Date: Jan. 26, 1998
(87) PCT Pub. No.: WO97/45107
   PCT Pub. Date: Dec. 4, 1997

(30) Foreign Application Priority Data

May 24, 1996 (JP) .................................................. 8-129458

(51) Int. Cl.[7] .............................. C12P 17/00; C12P 13/12
(52) U.S. Cl. .......................... 514/19; 435/115; 435/116; 435/117; 435/118; 435/113; 514/18; 514/19; 514/706; 514/708; 514/709; 514/710; 514/712; 514/713; 562/553; 562/556; 562/557; 562/433; 424/570

(58) Field of Search ...................................... 562/553, 556, 562/557, 433; 514/2, 12, 18, 19, 706, 708, 709, 710, 713; 435/113, 115–118; 424/570

(56) References Cited

U.S. PATENT DOCUMENTS 3,950,387 * 4/1976 Joullié et al. ........................ 424/314

OTHER PUBLICATIONS

Block B. "The Chemistry of Garlic and Onions" Sci. Am. 252, 114–119, 1985.*

* cited by examiner

Primary Examiner—F. T. Moezie
(74) Attorney, Agent, or Firm—Oblon, Spivak, McClelland, Maier & Neustadt, P.C.

(57) ABSTRACT

The present invention discloses the use, in the manufacture of a preventive and therapeutic drug of a brain disease, of a compound represented by formula (1):

$$CH_2=CH-CH_2-S(O)_n-R \qquad (1)$$

[wherein R represents a hydrogen atom, an alkyl group, an alkenyl group, a substituted alkyl group, a substituted alkenyl group, an alkylthio group, an alkenylthio group, a phenyl group, a substituted phenyl group, a heterocyclic group, or a group derived from an amino acid or an oligopeptide by deletion of one hydrogen atom, and which group may have a protective group; and n is 0, 1, or 2], a glycoside thereof, or a salt of the compound or the glycoside.

The drug of the present invention for ameliorating brain diseases, inhibiting reduction of brain neurons and promoting branching of neurites, is useful for the prevention and treatment of brain diseases such as dementia in association with degeneration and sloughing of brain neurons.

5 Claims, 1 Drawing Sheet

IN VIVO METHOD OF IMPROVING SURVIVAL RATE OF BRAIN NEURONS

This application claims the benefit of international application no. PCT/JP97/01733, filed May 23, 1997.

TECHNICAL FIELD

The present invention relates to a drug for ameliorating brain diseases, and more particularly to a drug for ameliorating brain diseases useful for the prevention and treatment of cerebral function disorders, such as dementia, caused by degeneration and sloughing of brain neurons.

BACKGROUND ART

In recent years, among intrinsic diseases that occur as age increases, brain diseases led by Alzheimer's disease have come to be great social problems. In the human brain, several tens of billions of neurons form complicated neurological circuits in which the terminal of a neurite of a neuron transmits information at the junctional portion called a synapse by the mediation of a neurotransmitter. Almost all brain disorders are considered to be caused by the destruction of neurological circuits due to degeneration or sloughing of neurons. As is widely accepted, neurons that have matured can no longer undergo cell division. Therefore, needless to say, damage to neurons considerably affects maintenance of brain functions.

Recently, substances that participate in differentiation and growth of nerve tissue have been searched for in the living body, and several in vivo hormones have already been clarified to be active substances.

However, it has been pointed out that these hormones disturb the in vivo hormone balance when used at a concentration where they exhibits their activity on neurons, and therefore in actual use they are problematic for administration. In view of the foregoing, there is a strong need for the development of extracorporeally derived pharmaceuticals that are effective in the prevention of damage to neurons, particularly prevention or treatment of degeneration and sloughing of neurons.

Accordingly, the object of the present invention is to provide a drug for treating brain diseases, which drug enables prevention or treatment of dementia and similar diseases caused by degeneration or sloughing of neurons.

DISCLOSURE OF THE INVENTION

The present inventors have conducted a screening of a wide variety of compounds originating from plants, and have discovered that certain compounds contained in garlic or preparations of processed garlic sulfur—amino acids having an allyl group and their analogs—inhibit decrease in brain neurons and promote branching of neurites, and therefore are useful as drugs for the treatment of brain diseases such as dementia caused in association with degeneration and sloughing of brain neurons. The present invention has been accomplished based on this finding.

Accordingly, the present invention provides the use in the manufacture of a preventive and therapeutic drug of brain diseases of a compound represented by the following formula:

  (1)

[wherein R represents a hydrogen atom, an alkyl group, an alkenyl group, a substituted alkyl group, a substituted alkenyl group, an alkylthio group, an alkenylthio group, a phenyl group, a substituted phenyl group, a heterocyclic group, or a group which is derived from an amino acid or an oligopeptide by deletion of one hydrogen atom, and which group may have a protective group; and n is 0, 1, or 2], a glycoside thereof, or a salt of the compound or the glycoside.

The present invention also provides a method for the treatment of brain diseases characterized by administering an effective amount of the compound of formula (1), a glycoside thereof, or a salt of the compound or the glycoside.

BEST MODE FOR CARRYING OUT THE INVENTION

Figure 1:
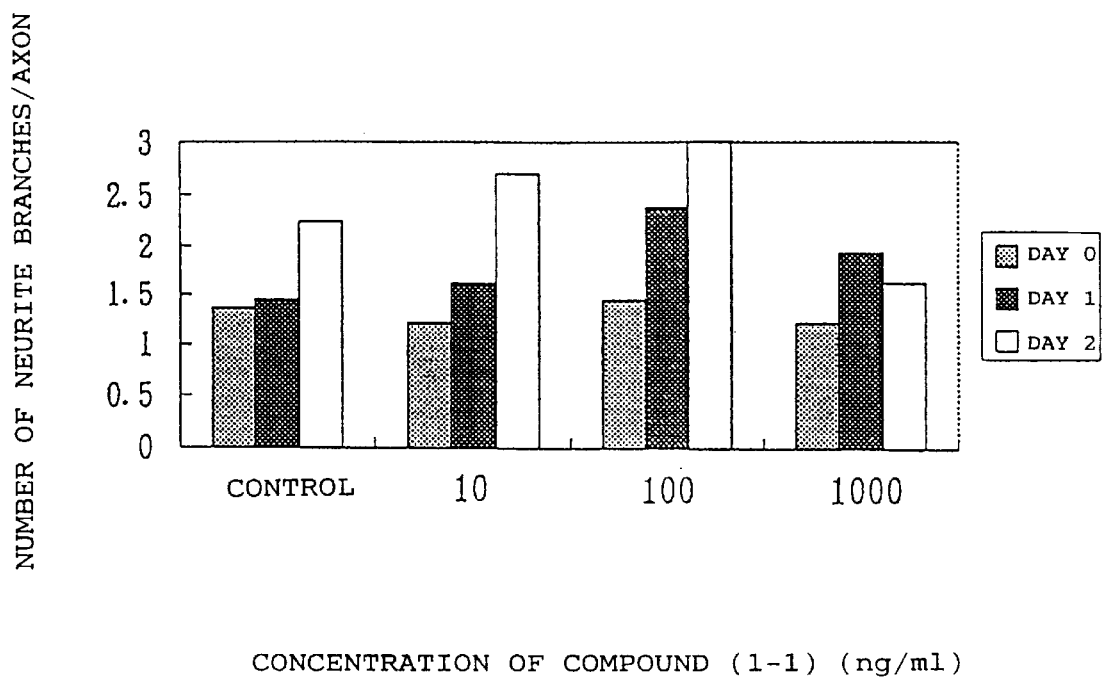
FIG. 1 shows the branching promotion effect of compound (1-1) on neurites.

Regarding R in the above-described formula (1), examples of the alkyl group include linear or branched C1–C6 alkyl groups. Specifically, mention may be given of a methyl group, an ethyl group, a n-propyl group, an isopropyl group, a n-butyl group, an isobutyl group, a n-pentyl group, and a n-hexyl group. Examples of the alkenyl group include linear or branched C2–C6 alkenyl groups. Specifically, mention may be given of a vinyl group, an allyl group, a 1-propenyl group, a butenyl group, and a pentenyl group. Examples of the substituted alkyl and substituted alkenyl groups include those corresponding to the above-mentioned alkyl or alkenyl groups which are substituted by a hydroxyl group, an amino group, a carboxyl group, a halogen atom, etc. Examples of the alkylthio group and the alkenylthio group include those resulting from linkage of a thio group to the above-mentioned alkyl group (s) or alkenyl groups(s). Examples of the substituted phenyl group include phenyl groups which are substituted by a hydroxyl group, an amino group, a carboxyl group, a lower alkyl group, a halogen atom, etc. Examples of the heterocycle include a group having nitrogen, oxygen, sulfur, etc. in the ring; such as oxazolyl group and benzoxazolyl group. Regarding the group which is derived from an amino acid by deletion of one hydrogen atom, examples of the amino acid include amino acids such as glycine, leucine, valine, alanine, and phenylalanine; as well as sulfur-containing amino acids such as cysteine and homocysteine. Regarding the group which is derived from an oligopeptide by deletion of one hydrogen atom, examples of the oligopeptide include combinations of two to several amino acids, more specifically, alanyl-alanine, glutamyl-glycine, and glutamyl-cysteinyl-glycine. The group which is derived from an amino acid or oligopeptide by deletion of one hydrogen atom encompasses those groups in which the functional groups are protected by lower acyl groups or lower aralkyl groups in accordance with customary methods in the peptide chemistry.

In formula (1), R is preferably a hydrogen atom, an alkyl group, an alkenyl group, a substituted alkyl group, a substituted alkenyl group, an alkylthio group, an alkenylthio group, or a group derived from an amino acid or oligopeptide by deletion of one hydrogen atom, which group may have a protective group. Particularly, the groups represented by the following formula (2) are preferred:

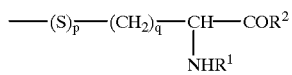 (2)

[wherein $R^1$ represents a hydrogen atom, a lower acyl group, a lower aralkyl group, an amino acid residue, or a polypeptide residue; $R^2$ represents a hydroxyl group, an amino acid residue, or a polypeptide residue; p represents 0 or 1, and q represents 1 or 2].

In formula (1), "—$S(O)_n$—" represents a thio group when n=0, a sulfinyl group when n=1, and a sulfonyl group when n=2.

Compounds (1) and saccharides may together form glycosides. The present invention encompasses such compounds. Examples of saccharides include monosaccharides such as fructose, glucose, and xylose; disaccharides such as sucrose and gentiobiose; and oligo saccharides formed of several monosaccharides linked to each other. Compounds (1) may also form acid addition salts or base addition salts together with arbitrary acids or bases. The resultant salts are within the scope of the present invention. Examples of acid addition salts include (a) salts formed with mineral acids such as hydrochloric acid and sulfuric acid, (b) salts formed with organic carboxylic acids such as formic acid and citric acid, (c) salts formed with sulfonic acids such as methanesulfonic acid and benzenesulfonic acid. Examples of base addition salts include (a) salts formed with alkali metals such as sodium and potassium, (b) salts formed with alkaline earth metals such as calcium and magnesium, (c) salts formed with nitrogen-containing organic bases such as ammonium and triethylamine.

Specific examples of compounds (1) used in the present invention include the following:

Compound (1-1): S-allyl-L-cysteine
$CH_2$=$CH$—$CH_2$—$S$—$CH_2CHCOOH$
　　　　　　　　　　　　　　|
　　　　　　　　　　　　　　$NH_2$ Compound (1-2): S-allyl-L-cysteine sulfoxide
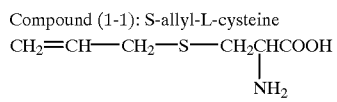

Compound (1-3): S-allylsulfonyl-L-alanine
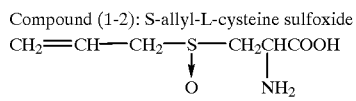

Compound (1-4): S-allyl-L-mercaptocysteine
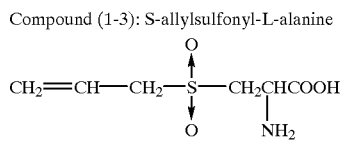

Compound (1-5): N-acetyl-S-allyl-L-cysteine
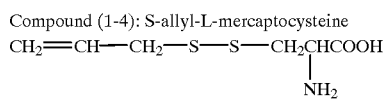

Compound (1-6): gamma-glutamyl-S-allyl-L-cysteine
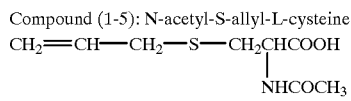

Compound (1-7): S-allylglutathione
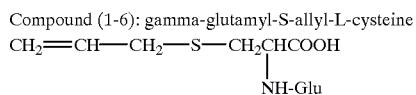
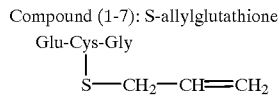

Compound (1-8): fructosyl-S-allyl-L-cysteine
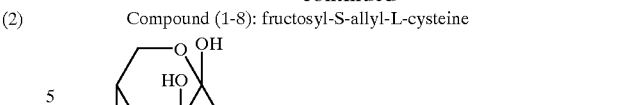

Compound (1-9): S-allyl-L-homocysteine
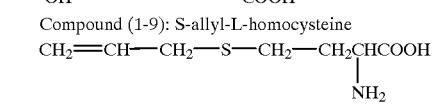

Compound (1-10): allyl mercaptane
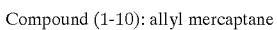

Compound (1-11): diallyl sulfide
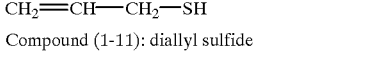

Compound (1-12): diallyl disulfide
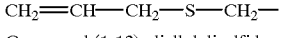

Compound (1-13): S-allylthiomalic acid
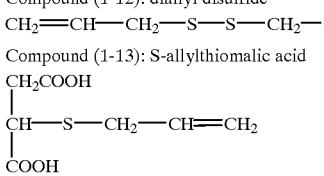

Compound (1-14): S-allylthiosalicylic acid
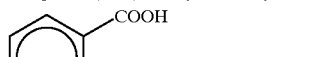

Compound (1-15): S-allylthiobenzoxazole
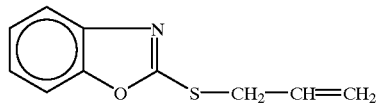

Of all compounds (1), compounds (1-2) and (1-6) are naturally occurring amino acid and peptide contained in crude garlic, and therefore, they can be obtained from the crude garlic. Compounds other than (1-2) and (1-6) compounds may also be obtained by use of known methods (Phytochemistry, 24(7), 1593–1594 (1985) and their citations).

As will be described hereinbelow in the "Examples" section, compounds (1) and glycosides or salts thereof exhibit inhibitory effect against reduction in brain neurons and branching promotion effect on neurites. Therefore, the compounds are useful for the prevention and treatment of brain diseases such as dementia caused by the degeneration and sloughing of brain neurons.

Regarding the toxicity of compounds (1-1), in view that $LD_{50}$ values with rats and mice in the case of oral administration are not less than 1,000 mg/kg, the compounds (1) of the present invention are determined to be low toxic in general.

The drugs of the present invention for treating brain diseases may be in the form of the aforementioned compounds (1) or glycosides or salts thereof per se, or may be prepared by incorporating the aforementioned compounds (1) or glycosides or salts thereof into pharmaceutically-acceptable carriers such as a pharmaceutical vehicle, binder, and a diluent. They can be prepared into oral or parenteral preparations of arbitrary physical shapes, including powders, granules, tablets, capsules, syrups, and injections. Needless to say, other drugs may also be incorporated.

The dose of the drugs of the present invention for treating brain diseases may vary in accordance with the age, body weight, symptom, etc. In the case of oral administration, the drug of the invention is preferably administered in an amount of 1 mg–5 g, more preferably 1 mg–1 g per day, in terms of the weight of compound (1). According to a preferred mode of the present invention, the drug has a unit dosage form allowing administration of the above-mentioned daily dosage at a single time or in divided times.

EXAMPLES

The present invention will next be described in detail by way of examples, which should not be construed as limiting the invention thereto.

Example 1

Effect of Compounds (1-1) Through (1-15) to Inhibit Reduction in Survival Rate of Neurons From a rat at the 18th day of pregnancy (having an 18-day old embryo) the uterus was aseptically removed under etherification, and the fetus was obtained. The whole brain was collected from the fetus. From the brain placed in an L-15 medium, the hippocampus was separated under a microscope and minced with a knife. The minced hippocampus was treated by the addition of trypsin (0.25%) and Dnase (0.01%) for 30 minutes at 37° C. to thereby isolate cells. The thus-isolated cells were suspended in Eagle's MEM medium supplemented with 10% fetal calf serum, and inoculated at a concentration of $4 \times 10^4$ cells/cm$^2$ into wells of a 48-well plate which had been coated with poly-L-lysin in advance. Following incubation for 24 hours, the medium was replaced by a serum-free DMEM/F-12 medium containing compound (1) at different concentrations. After three-days' additional incubation, the cells were fixed, stained, and the number of surviving cells in each well was counted. The number was compared with the number obtained from the control group in which compound (1) was not added. The results are shown in Table 1.

TABLE 1

Effect of compounds (1) to inhibit reduction in survival rate of neurons

| Compound | Concentration (g/ml) | | | | |
|---|---|---|---|---|---|
| | $10^{-10}$ | $10^{-9}$ | $10^{-8}$ | $10^{-7}$ | $10^{-6}$ |
| (1-1) | ± | ↑ | ↑↑ | ↑↑ | ↑ |
| (1-2) | ± | ↑ | ↑↑ | ↑↑ | ↑ |
| (1-3) | | ↑ | ↑ | ↑↑ | ↑ |
| (1-4) | ± | ± | ↑ | ↑↑ | ± |
| (1-5) | | ± | ↑ | ↑ | ↑ |
| (1-6) | ± | ± | ↑↑ | ↑↑ | ↑↑ |
| (1-7) | ± | ± | ± | ↑↑ | ↑↑ |
| (1-8) | | | ↑ | ↑↑ | ↑ |
| (1-9) | | | ± | ↑ | ± |
| (1-10) | ± | ± | ↑ | ↑↑ | |
| (1-11) | ± | ± | ↑ | ↑↑ | |
| (1-12) | ± | ± | ↑ | ↑ | |
| (1-13) | | | ± | ↑ | ↑ |
| (1-14) | | | ± | ↑ | ↑ |
| (1-15) | | | ± | ↑ | ↑ |

When the survival rate of the neurons in the control group was taken as 100%:

±: 90~110%, ↑: 110~130%, ↑↑: 130~150%

In the control group, the number of surviving cells among the isolated cells that were inoculated at a concentration of $4 \times 10^4$ cells/cm$^2$ decreased to as low as to $1 \times 10^4$ cells/cm$^2$ on the third day of incubation with the serum-free medium. In contrast, as shown in Table 1, compounds (1-1) through (1-15) exhibited effect of inhibiting reduction of neurons within the concentration range of 1–1,000 ng/ml, although activity differed from compound to compound (activity of control: 100%).

As structural comparative compounds, the following compounds were tested for activity: compounds in which an allyl group is linked to an atom other than a sulfur atom—i.e, allyl alcohol, diallyl ether, O-allyl-L-cysteine, allyl glycine, eugenol, N-allyl urea—and compounds in which a substituent (including a hydrogen atom) other than an allyl group is linked to a sulfur atom—i.e, dipropylsulfide, dipropyldisulfide, L-cysteine, glutathione, S-methyl-L-cysteine, S-propyl-L-cysteine, S-methyl-L-cysteinesulfoxide, gamma-glutamyl-S-propyl-L-cysteine, S-(1-propenyl)-L-cysteine, S-propargyl-L-cysteine, and S-(3-butenyl)-L-cysteine. No inhibitory effect against reduction in survival rate of hippocampus neurons was found in any of these compounds within the range of 1–1,000 ng/ml. From this, it has become clear that the presence of a thioallyl group, an allylsulfinyl group, or an allylsulfonyl group is required as an essential structure for the manifestation of activity.

Example 2

Branching Promotion Effect of Compound (1-1) on Neurites

The hippocampus cells obtained in a manner similar to that in Example 1 were incubated for 24 hours in a medium containing fetal calf serum, then for further 24 hours in a serum-free medium. Subsequently, compound (1-1) was added. When compound (1-1) was added, and at the times of one and two days after addition, photographs were taken of the same cells. The number of branches from the longest neurite was counted.

As a result, as shown in FIG. 1, compound (1-1) was confirmed to have branching promotion effect on neurites.

INDUSTRIAL APPLICABILITY

The drug of the present invention for ameliorating brain diseases, inhibiting reduction of brain neurons and promoting branching of neurites, is useful for the prevention and treatment of brain diseases such as dementia in association with degeneration and sloughing of brain neurons.

What is claimed is:
1. A method of inhibiting reduction in the survival rate of brain neurons which comprises contacting the neurons with an effective amount of a compound of the formula (I):

$$CH_2=CH-CH_2S(O)_n-R \quad (I)$$

wherein R represents a hydrogen atom; a $C_{1-6}$ alkyl group optionally substituted with a hydroxyl, amino, carboxyl or halogen atom; a $C_{2-6}$ alkenyl group optionally substituted with a hydroxyl, amino, carboxyl or halogen atom; a $C_{1-6}$ alkylthio group optionally substituted with a hydroxyl, amino, carboxyl or halogen atom; a $C_{2-6}$ alkenylthio group optionally substituted with a hydroxyl, amino, carboxyl or halogen atom; a phenyl group optionally substituted with a hydroxyl, amino, carboxyl, lower alkyl or halogen atom; a heterocyclic group selected from oxazolyl or benzoxazolyl; an amino acid residue selected from glycinyl, leucinyl, valinyl, alaninyl, phenylalaninyl, cysteinyl or homocysteinyl optionally having a protective group; an oligopeptide residue selected from alanyl-alanine, glutamyl-glycine or glutamyl-cysteinyl-glycine optionally having a protective group; a glycoside obtained by reacting a compound of the above formula (I) with saccharide; or salts of the above, wherein n is 0, 1 or 2.

2. A method according to claim 1, wherein in formula (I), R represents a hydrogen atom, an alkyl group of 1 to 6 carbon atoms optionally substituted with a hydroxyl, amino, carboxyl or halogen atom, an alkenyl group of 2 to 6 carbon atoms optionally substituted with hydroxyl, amino, carboxyl or halogen atom, a $C_{1-6}$ alkylthio group, a $C_{2-6}$ alkenylthio group, an amino acid residue selected from gylcinyl, leucinyl, valinyl, alaninyl, phenylalaninyl, cysteinyl or homocysteinyl optionally having a protective group or an oligopeptide residue selected from alanyl-alanine, glutamyl-glycine or glutamyl-cysteinyl-glycine optionally having a protective group.

3. A method according to claim 1, wherein said compounds of formula (I) is selected from the group consisting of S-allyl-L-cysteine, S-allyl-L-cysteine sulfoxide, S-allylsulfonyl-L-alanine, S-allyl-L-mercaptocysteine, N-acetyl-S-allyl-L-cysteine, gamma-glutamyl-S-allyl-L-cysteine, S-allylglutathione, fructosyl-S-allyl-L-cysteine, S-allyl-L-homocysteine, allyl mercaptane, diallyl sulfide, diallyl disulfide, S-allylthiomalic acid, S-allylthiosalicylic acid and S-allylthiobenzoxazole.

4. A method according to claim 1, wherein the compound of formula (1) is S-allyl-L-cysteine.

5. A method according to claim 1 wherein in formula (I), R has the following formula (2):

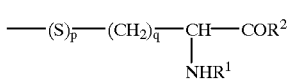

(2)

wherein $R^1$ represents a hydrogen atom, a lower acyl group, a lower aralkyl group, an amino acid residue, or a polypeptide residue; $R^2$ represents a hydroxyl group, an amino acid residue, or a polypeptide residue; p represents 0 or 1, and q represents 1 or 2, said amino acid residue being selected from glycinyl, leucinyl, valinyl, alaninyl, phenylalaninyl, cysteinyl or homocysteinyl and said polypeptide residue being selected from alanyl-alanine, glutamyl-glycine or glutamyl-cysteinyl-glycine.

* * * * *